United States Patent
Ho et al.

(10) Patent No.: US 10,426,603 B2
(45) Date of Patent: Oct. 1, 2019

(54) METHODS AND APPARATUS FOR TREATING GLOTTIC INSUFFICIENCY

(71) Applicant: APREVENT MEDICAL INC., Grand Cayman (KY)

(72) Inventors: Guan-Min Ho, Milpitas, CA (US); Chia-Yuan Chang, Milpitas, CA (US)

(73) Assignee: APREVENT MEDICAL INC. (KY)

(*) Notice: Subject to any disclaimer, the term of this patent is extended or adjusted under 35 U.S.C. 154(b) by 0 days.

(21) Appl. No.: 15/550,033

(22) PCT Filed: Apr. 7, 2017

(86) PCT No.: PCT/US2017/026724
§ 371 (c)(1),
(2) Date: Aug. 10, 2017

(87) PCT Pub. No.: WO2017/177208
PCT Pub. Date: Oct. 12, 2017

(65) Prior Publication Data
US 2018/0064532 A1 Mar. 8, 2018

Related U.S. Application Data

(60) Provisional application No. 62/455,515, filed on Feb. 6, 2017, provisional application No. 62/419,972, filed
(Continued)

(51) Int. Cl.
*A61F 2/20* (2006.01)
*A61F 5/56* (2006.01)

(52) U.S. Cl.
CPC ............... *A61F 2/20* (2013.01); *A61F 5/566* (2013.01); *A61F 2220/0008* (2013.01);
(Continued)

(58) Field of Classification Search
CPC ............... A61F 2/20; A61F 2250/0096; A61F 2250/0003; A61F 2220/0008;
(Continued)

(56) References Cited

U.S. PATENT DOCUMENTS

| 5,197,982 A | 3/1993 | Goldsmith, III et al. |
| 5,306,298 A * | 4/1994 | Godley, III ............... A61F 2/20 623/9 |

(Continued)

FOREIGN PATENT DOCUMENTS

| CN | 104918581 A | 9/2015 |
| EP | 0078685 A1 | 5/1983 |

(Continued)

OTHER PUBLICATIONS

Shah et al. "Imaging of Common Breast Implants and Implant-Related Complications: A Pictorial Essay." Indian Journal of Radiology and Imaging, vol. 26, No. 2, 2016, p. 216.*

(Continued)

*Primary Examiner* — Leslie Lopez
(74) *Attorney, Agent, or Firm* — Su IP Consulting

(57) ABSTRACT

An example implant system to treat glottic insufficiency is disclosed. The implant system includes a fixation frame including a first set of flanges at a first edge of the fixation frame and a second flange at a second edge of the fixation frame, wherein the fixation frame is configured to secure the implant system at an opening of the patient's thyroid cartilage, a port system disposed in the fixation frame and configured to receive, deliver, maintain, or remove a filler, and a flexible member, coupled to the fixation frame and in fluid or air communication with the port system, wherein based on an amount of the filler in the flexible member, the flexible member is configured to inflate in a direction to push against the patient's arytenoid cartilage so the arytenoid cartilage is rocked, adducted and/or rotated inferomedially.

19 Claims, 14 Drawing Sheets

Related U.S. Application Data on Nov. 10, 2016, provisional application No. 62/341,610, filed on May 25, 2016, provisional application No. 62/320,444, filed on Apr. 8, 2016.

(52) U.S. Cl.
CPC ............... *A61F 2220/0041* (2013.01); *A61F 2250/0003* (2013.01); *A61F 2250/0004* (2013.01); *A61F 2250/0018* (2013.01); *A61F 2250/0096* (2013.01)

(58) Field of Classification Search
CPC ...... A61F 2220/0041; A61F 2250/0018; A61F 2250/0004; A61F 5/566
See application file for complete search history.

(56) References Cited

U.S. PATENT DOCUMENTS

| | | |
|---|---|---|
| 5,549,673 A | 8/1996 | Beale |
| 9,204,963 B2 | 12/2015 | Reif et al. |
| 9,700,408 B1 * | 7/2017 | Sataloff ............... A61F 2/20 |
| 2004/0254642 A1 * | 12/2004 | Isshiki ................ A61F 2/20 623/11.11 |
| 2011/0301580 A1 | 12/2011 | Hoffman |
| 2012/0150293 A1 * | 6/2012 | Hoffman .............. A61F 2/20 623/9 |
| 2013/0281973 A1 | 10/2013 | McCulloch et al. |
| 2013/0294613 A1 | 11/2013 | Nagel et al. |

FOREIGN PATENT DOCUMENTS

| | | |
|---|---|---|
| WO | 2014145327 A1 | 9/2014 |
| WO | 2016039810 A1 | 3/2016 |

OTHER PUBLICATIONS

International Search Report and Written Opinion of the International Searching Authority, International application No. PCT/US2017/026724, dated Jun. 16, 2017.
The Extended European Search Report, application No. 17751225.8, dated Oct. 4, 2018.

* cited by examiner

METHODS AND APPARATUS FOR TREATING GLOTTIC INSUFFICIENCY

CROSS-REFERENCE TO RELATED APPLICATIONS

The present application is a U.S. National Stage filing under 35 U.S.C. § 371 of International Application PCT/US2017/026724, filed Apr. 7, 2017, which claims the benefit of U.S. Provisional Application No. 62/320,444, filed Apr. 8, 2016, U.S. Provisional Application No. 62/341,610, filed May 25, 2016, U.S. Provisional Application No. 62/419,972, filed Nov. 10, 2016, and U.S. Provisional Application No. 62/455,515, filed Feb. 6, 2017. The International Application and the U.S. Provisional Applications, including any appendices or attachments thereof, are incorporated by reference herein in their entirety.

BACKGROUND

Dysphagia associated with aspiration pneumonia often occurs in patients with neurological disorders. The neurological disorders may be caused by stroke, brain surgery, head and/or spinal cord trauma, oropharyngeal diseases, radiation therapy, cardiac/thoracic surgery, autoimmune or other degenerative neurologic diseases. The aspiration pneumonia may be mainly caused by glottic insufficiency, due to vocal fold paralysis with or without swallowing dysfunction. Stroke patients with aspiration symptoms may have a seven-time higher risk in developing aspiration pneumonia than other types of patients. For these stroke patients, even after recovery, there is still a relatively high incidence of dysphagia associated with aspiration pneumonia.

Conventional surgical techniques to treat dysphagia and glottic insufficiency may include Type I Medialization Thyroplasty (MT) procedure and Arytenoid Adduction (AA) procedure. Type I MT procedure is the main phonosurgical procedure performed in patients with glottic insufficiency. The primary limitations of Type I MT procedure include the inability to close a wide posterior glottal chink and restore the physiological swallowing steps, like laryngeal elevation and vocal fold movement. For patients with vocal fold paralysis and a significant posterior glottic gap after the Type I MT procedure, an AA procedure may be performed subsequently to close the incompletely closed posterior glottis. Still, one limitation of the AA procedure, associated with the posterior airway closure, is an increased frequency of postoperative airway complaints after the AA procedure, due to postoperative tissue edema in the glottic area. Further, Type I MT and AA procedures may not be suitable for patients having difficulty with prolonged periods of supine positioning or intolerable for long lasting surgical procedures.

Since the above two procedures either use implants or suture fixation technique, a common complaint from these procedures is the inability to precisely adjust the implant or sutures intraoperatively and postoperatively. Specifically, it is difficult to accurately perform intraoperative adjustment of implant due to edematous swelling of laryngeal mucosa caused by these procedures. For example, carving an implant during surgery may result in prolonged operation time and suboptimal shaping of the implant. Furthermore, these implants cannot be postoperatively adjusted at all.

Providing an adjustable implant for the procedure would shorten the operation time, and reduce the risk of postoperative airway compromise. The size of the adjustable implant would be customized for each individual's needs, from which the patient could greatly benefit.

SUMMARY

In some embodiments of the present disclosure, an implant system to treat glottic insufficiency is disclosed. The implant system includes a fixation frame comprising a first set of flanges at a first edge of the fixation frame and a second flange at a second edge of the fixation frame, wherein the fixation frame is configured to secure the implant system at an opening of the patient's thyroid cartilage, a port system disposed in the fixation frame and configured to receive, deliver, maintain, or remove a filler, and a flexible member, coupled to the fixation frame and in fluid or air communication with the port system, wherein based on an amount of the filler in the flexible member, the flexible member is configured to inflate in a direction to push against the patient's arytenoid cartilage so the arytenoid cartilage is rocked, adducted and/or inferomedially rotated.

In some other embodiments of the present disclosure, a method to treat glottic insufficiency of a patient is disclosed. The method includes placing an implant system in an opening of the patient's thyroid cartilage, attaching a fixation plate and a fastener to a fixation frame of the implant system, wherein a thread goes through one or more holes of the fixation plate, securing the implant system on the thyroid cartilage with the fixation plate and the fastener, guiding an injector to a port system of the implant system, and injecting an amount of a filler to inflate a flexible member of the implant system so the flexible member pushes against the patient's arytenoid cartilage and rocks, adducts, and/or inferomedially rotates the patient's arytenoid cartilage.

DETAILED DESCRIPTION

Figure 1A:
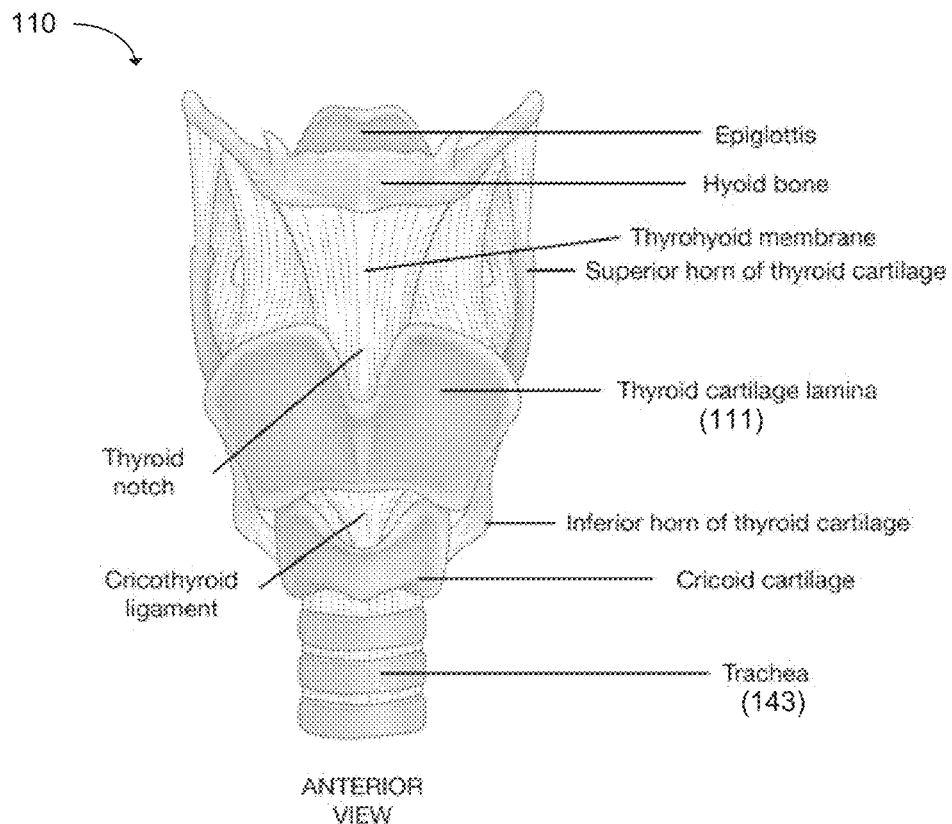
FIGS. 1A and 1B illustrate various views of larynx anatomy.
Figure 1A:
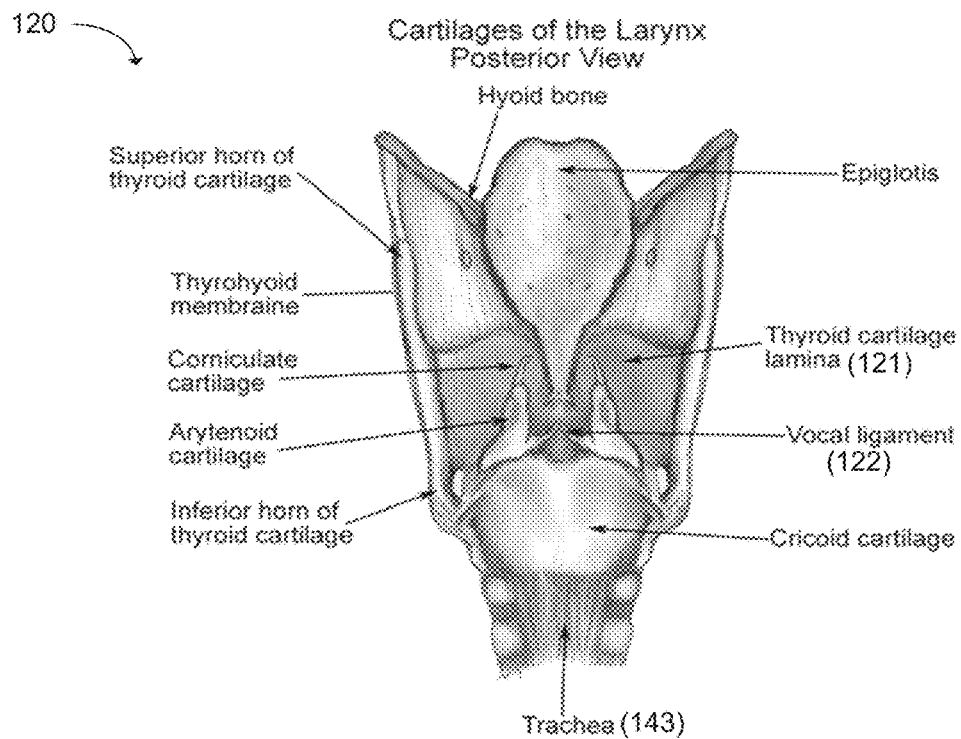

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated herein.

The present disclosure describes apparatuses and methods to treat glottic insufficiency (due to neuromuscular incoordination or disordered interaction (cooperation) between the intrinsic muscles), and the poor closure of larynx inlet (opening) (due to uncoordinated bending of epiglottis and delayed or absence of laryngeal elevation). The disclosed treatments may improve the glottic closure and reduce the incidence of aspiration, thus preventing the aspiration's sequelae, such as aspiration pneumonia. Furthermore, the disclosed treatments may enable the postoperative adjustment of implants, and reduce the risk of postoperative airway compromise. As a result, the disclosed treatments may shorten the operation time during the surgical procedures. Perioperative complications, such as difficult intubation, can also be prevented through the implant adjustability. With a complete glottic closure, aspiration pneumonia can be effectively reduced or prevented after the surgical procedures.

In examples of the present disclosure, an implant system is designed to close the glottis by rocking, adducting, or inferomedially rotating the arytenoid cartilage. The amount of rock, adduction and/or inferomedially rotation is adjustable by changing the size of an implant, and the size of the implant can be changed by varying the amount of filler in the implant. The present disclosure may achieve the same effect as type I Medialization Thyroplasty (MT) and Arytenoid Adduction (AA), when performed together. Further, it may lengthen and tense the vocal fold by posterior expansion of the flexible member.

Figure 1B:
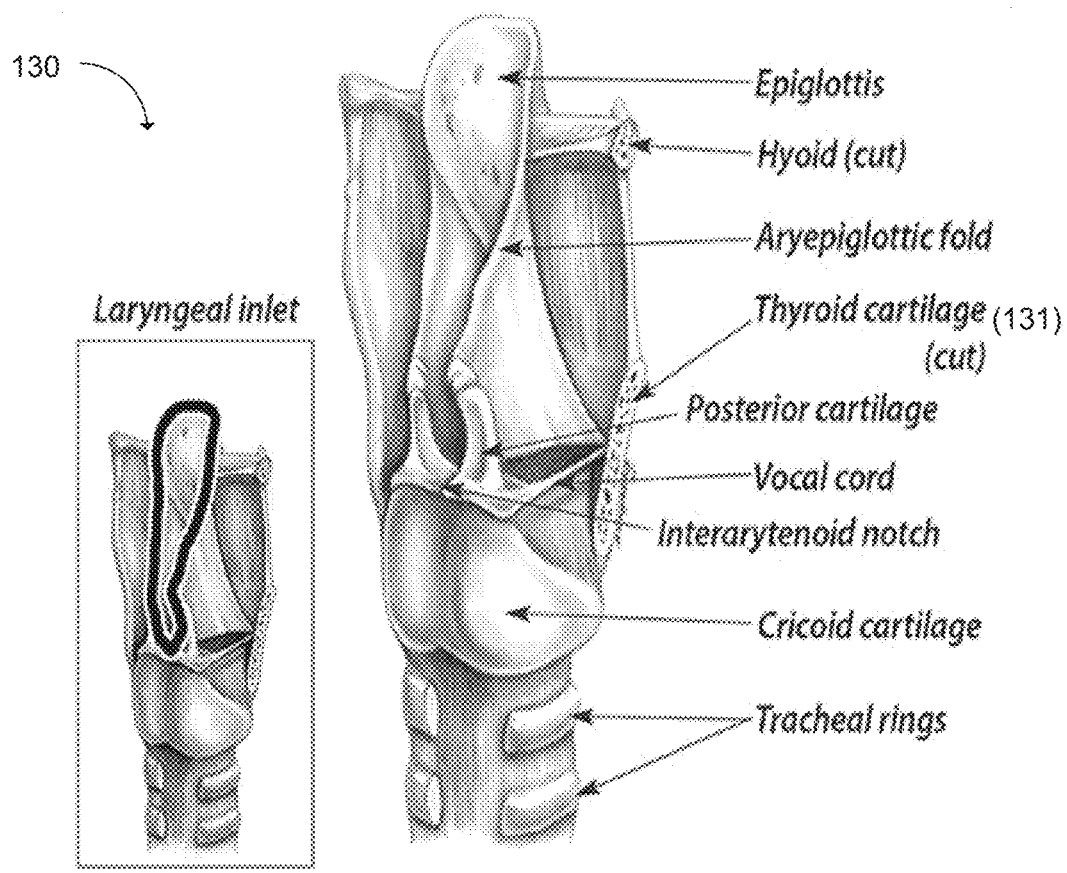

FIGS. 1A and 1B illustrate various views of larynx anatomy.

Drawing 110 shows the anatomy of a patient's larynx in an anterior view, with outer side 111 of the thyroid cartilage, or the thyroid cartilage lamina, exposed. Drawing 120 shows the same patient's larynx in a posterior view, with inner side 121 of the thyroid cartilage exposed. Drawing 120 further shows the patient's vocal ligament 122, which are enclosed within the patient's vocal folds (not shown in the drawing 120). Drawing 130 shows the same patient's laryngeal cartilages (including a cross-sectional view 131 of the thyroid cartilage) in an angled lateral view. In examples of the present disclosure, the space surrounded by the laryngeal cartilages, including but not limited to thyroid cartilage, corniculate cartilage, arytenoid cartilage, cricoid cartilage, posterior cartilage illustrated in FIGS. 1A and 1B, as well as the tissues and organs connected to these cartilages, may be deemed a "paraglottic space." In other words, the paraglottic space may be a space bounded by the thyroid cartilage and the various surrounding membranes.

Figure 1C:
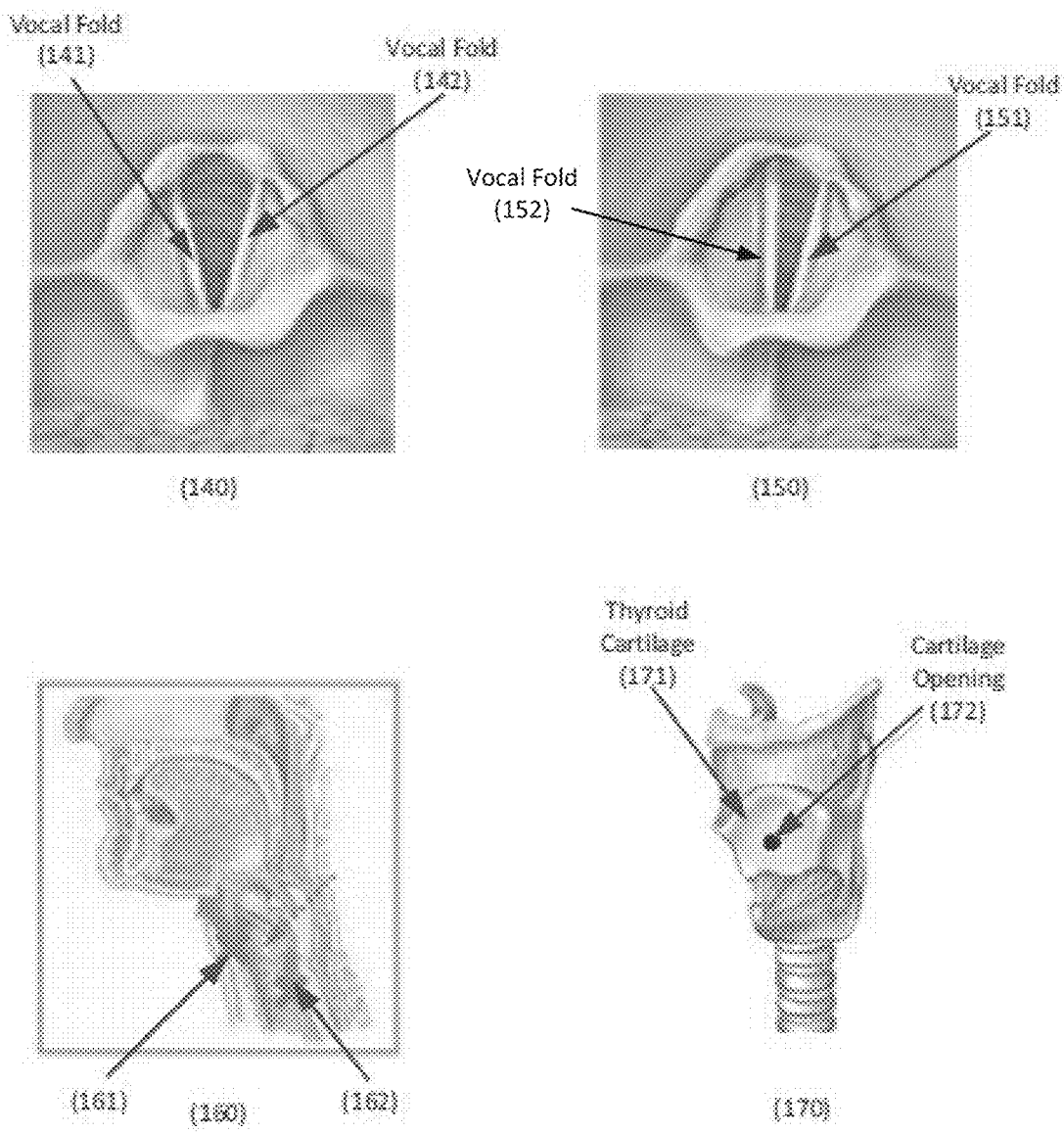
FIG. 1C illustrates various symptoms of glottic insufficiency.

FIG. 1C illustrates various symptoms of glottic insufficiency.

Drawing 140 illustrates an example healthy vocal fold having two lateralized vocal folds 141 and 142. During normal breathing, swallowing, or speaking, vocal folds 141 and 142 open and close in unison. Before a person swallows food, the food or drink is first crushed and/or mixed into a pasty mass known as a bolus. During swallowing, the person's extrinsic and intrinsic muscles cooperate to prevent food or drink from entering the glottis. For example, the person's extrinsic muscles elevate the larynx and bend the epiglottis over the entrance to the glottis so that the bolus can glide across the epiglottis rather than falling into the larynx. While this movement is under way, the person's intrinsic muscles close the glottis. In conjunction with FIG. 1A, should any food particles or liquids pass through the vestibule or vocal folds 141 and 142 or come in contact with trachea 143, a cough reflex may be automatically triggered in a healthy person to prevent the material from falling more caudally. However, this cough reflex is desensitized in patients with neurological disorder, such as stroke, making it more important to completely close the glottic gap.

Drawing 150 illustrates an example unhealthy vocal cord having a paralyzed vocal fold 151 unable to move to a fully lateralized/medialized position. In other words, paralyzed vocal fold 151 cannot be opened and closed in unison with the other vocal fold 152, leaving an opening or gap in the glottis. Thus, during swallowing, the bolus may inadvertently slip into the glottis and subsequently into the trachea, bronchus, and lungs, which may lead to infection and pneumonia. Further, as shown in drawing 160, for some of the stroke patients, due to impaired neurological stimulus, the trigger of epiglottis bending, the glottic closure 161, and/or the laryngeal elevation 162 are delayed or absent, leading to incoordination of their extrinsic and intrinsic muscle movements. As a result, the patient may have difficulty in swallowing and may even choke as well.

To treat a patient's glottic insufficiency and/or swallowing difficulty, drawing 170 shows that a surgeon or medical machinery may utilize a surgical device to create cartilage opening 172 in the patient's thyroid cartilage 171. The surgical device may perform certain functions such as drilling, shaping, space expansion (e.g., "dissection"), and instrument/implant delivery. Afterwards, the surgeon or the medical machinery places a conventional implant system through cartilage opening 172 into the paraglottic space behind the patient's thyroid cartilage 171.

Figure 2A:
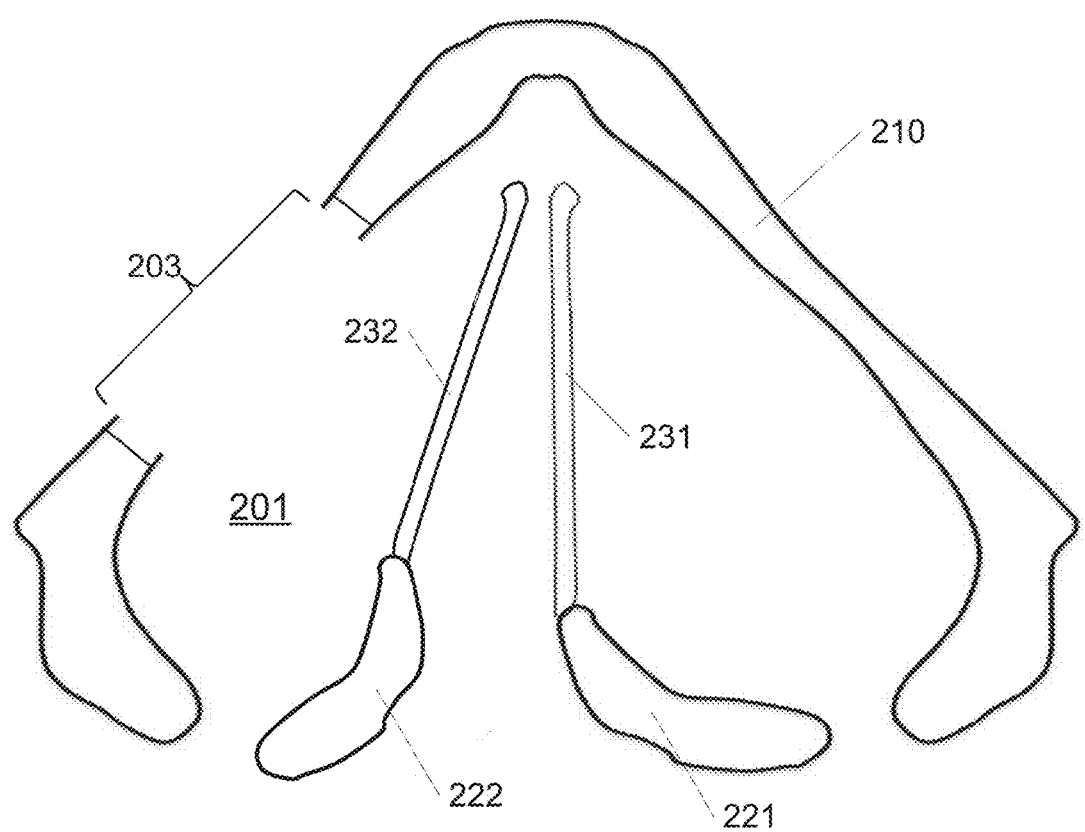
FIG. 2A illustrates a top view of a paraglottic space in which an implant system 200 can be placed to treat glottic insufficiency, in accordance with some embodiments of the present disclosure.

FIG. 2A illustrates a top view of paraglottic space 201 in which implant system 200 can be placed to treat glottic insufficiency, in accordance with some embodiments of the present disclosure. The top of the figure corresponds to the anterior aspect of a patient's larynx, and the bottom of the figure corresponds to the posterior aspect of the patient's larynx. In FIG. 2A, opening 203 of thyroid cartilage 210 is created to access paraglottic space 201 surrounded by thyroid cartilage 210 and arytenoid cartilages 221 and 222. Opening 203 and thyroid cartilage 210 may correspond to opening 172 and thyroid cartilage 171 of FIG. 1C, respectively. Arytenoid cartilage 221 is coupled to healthy vocal fold 231, and arytenoid cartilage 222 is coupled to paralyzed vocal fold 232. Opening 203 may be created with a surgical device on the patient's thyroid cartilage lamina. The surgical device may perform certain functions such as, without limitation, drilling, shaping, and space expansion (e.g., dissection).

Figure 2B:
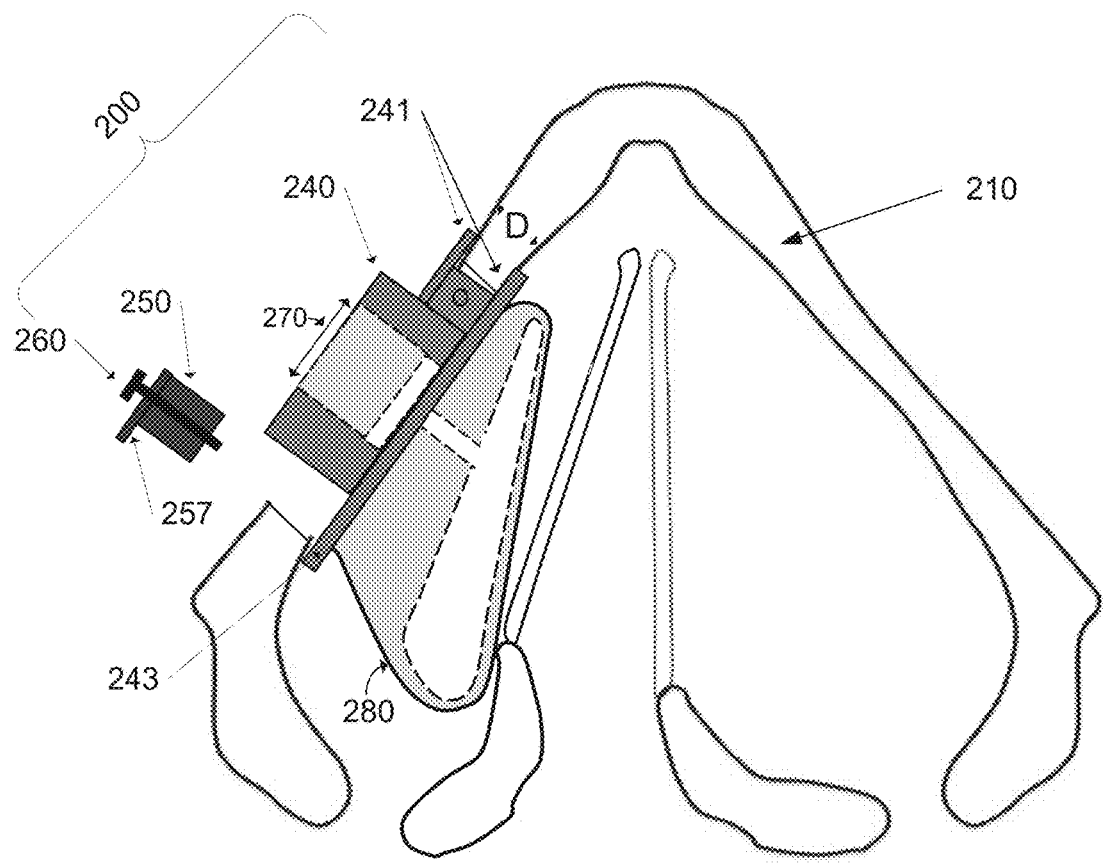
FIG. 2B illustrates an example implant system 200 to be placed in a paraglottic space through an opening of thyroid cartilage 203, in accordance with some embodiments of the present disclosure.

In conjunction with FIG. 2A, FIG. 2B illustrates an example implant system 200 to be placed in paraglottic space 201 through opening 203, in accordance with some embodiments of the present disclosure. Implant system 200 includes fixation frame 240, fixation block 250, fastener 260, port system 270, and flexible member 280. Implant system 200 may be secured to opening 203 with fixation frame 240. Fixation frame 240 includes a first set of flanges 241. Flanges 241 may be at a first edge of fixation frame 240, and they are separated from each other by a distance corresponding to the thickness D of thyroid cartilage 210 to engage fixation frame 240 with opening 203 of thyroid cartilage 210. This thickness D varies among patients. An example range of the thickness D is between 1 mm to 5 mm. Flanges 241 may or may not be substantially in parallel. Fixation frame 240 may include biocompatible materials, for example, titanium, peek, or silicone. In some other embodiments, fixation frame 240 may be elastic, so that it may be squeezed into and fit in various sizes of openings 203 of thyroid cartilage 210. In addition, removing or reinstalling an elastic fixation frame 240 may be easier. Fixation frame 240 may further include a second flange 243 at a second edge of fixation frame 240. Second flange 243 is configured to extend from the second edge of fixation frame 240, away from the first edge adjacent to flanges 241, to cover opening 203 of thyroid cartilage 210.

In some embodiments, fixation block 250 may include flange 257. Fixation block 250 may be secured with fixation frame 240 after fixation frame 240 is placed into opening 203. In some embodiments, fastener 260 is placed in fixation block 250 and is used to secure fixation block 250 to fixation frame 240. Fastener 260 is configured to secure with second flange 243 of fixation frame 240. Flange 257 and second flange 243 may be configured with a separation distance corresponding to the thickness D of thyroid cartilage 210 after fixation block 250 is secured with second flange 243 of fixation frame 240. In addition, fixation block 250 may have wings, extending in anterior, cranial and caudal directions, providing a better halt for fixation block 250 and preventing fixation block 250 from falling into paraglottic space 201 through opening 203.

Figure 2C:
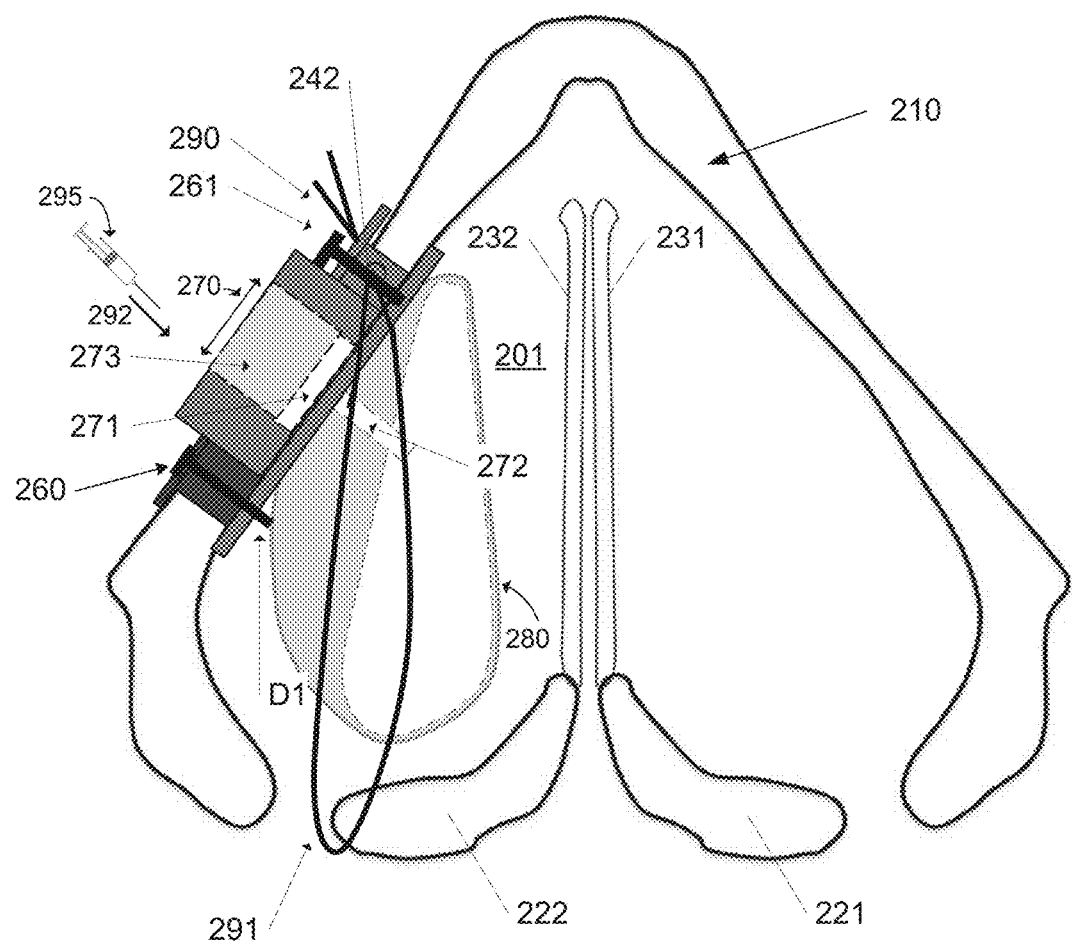
FIG. 2C illustrates an example implant system secured at an opening of a patient's thyroid cartilage and example approaches to rock, adduct, and/or inferomedially rotate the patient's arytenoid cartilage, in accordance with some embodiments of the present disclosure.

In conjunction with FIGS. 2A and 2B, FIG. 2C illustrates implant system 200 secured at opening 203 of thyroid cartilage 210 and example approaches to rock, adduct, and/or inferomedially rotate arytenoid cartilage, in accordance with some embodiments of the present disclosure. In some embodiments, by turning fastener 260, fastener 260 may protrude medially from second flange 243 with a distance D1 and be physically in contact with flexible member 280. As fastener 260 is turned further, fastener 260 may protrude further from second flange 243, and the distance D1 increases. D1 may be less than 5 mm. In other embodiments, D1 may be between 0 mm to about 4 mm. By pushing against flexible member 280 in a medial or medioposterior direction, the change in the position of flexible member 280 creates a physical contact between flexible member 280 and arytenoid cartilage 222 and initiates a clockwise rotation of arytenoid cartilage 222. This rotation leads to arytenoid cartilage 222 being rocked, adducted, and/or inferomedially rotated, which results in having the paralyzed vocal fold 232 fixed in its median position.

In alternative embodiments, if vocal fold 231 is paralyzed, an implant system similar to implant system 200 may be placed from a right opening (not shown but from the same perspective of FIG. 2C) of thyroid cartilage 210 to fix vocal fold 231 in its median position. A flexible member of the implant system may be pushed in medial or medioposterior direction, initiate a counterclockwise rotation of arytenoid cartilage 221, lead to arytenoid cartilage 221 being adducted and rotated inferomedially to fix vocal fold 231 in its median position.

The head of fastener 260 may be circular, non-circular with multiple angles, star-shaped, or any shape to provide a sufficient halt between fastener 260 and surrounding material. Fastener 260 may be rotated with a screwdriver manually or may be rotated by electromagnetic force or remote control (e.g. Bluetooth) with an actuator integrated in implant system 200.

In addition to using fastener 260 to adjust arytenoid cartilage 222, arytenoid cartilage 222 may also be adjusted with the AA surgical procedure. In some embodiments, fixation frame 240 provides a fixation point for one or more sutures used in the AA surgical procedure. One example of this fixation point may be a fastener. Fixation frame 240 may define opening 242. One or more sutures 290 can be inserted into opening 242 with one end 291 forming a loop to be in physical contact with the muscular process of the arytenoid cartilage 222 and/or lateral cricothyroid muscle and/or thyroarytenoid muscle to perform the AA surgical procedure. The other end of sutures 290 is secured on fastener 261 (e.g., screw) disposed adjacent to opening 242. A surgeon may fasten fastener 261 to adjust the length and tension of sutures 290. In response to the changes of the length and tension of sutures 290, traction forces exerted on intrinsic laryngeal adductor muscles and/or arytenoid cartilage results in a rotation of arytenoid cartilage 222, causing the change in the position in craniocaudal and/or mediolateral direction of a paralyzed vocal fold 232.

In addition to using fastener 260 and the AA surgical procedure, flexible member 280 may also be used to adjust arytenoid cartilage 222 and paralyzed vocal fold 232. In conjunction with FIGS. 2A and 2B, in some embodiments, port system 270 is an apparatus configured to receive, deliver, maintain, or remove a filler (e.g., saline solution) to inflate or deflate flexible member 280. In some embodiments, port system 270 includes port membrane 273, port chamber 271, and flow channel 272. Port system 270 may be disposed in fixation frame 240. To access port system 270, a healthcare professional may use an injector, such as injector 295, in direction 292 to puncture port membrane 273. The filler may be injected into port system 270 after injector 295 reaches port chamber 271. In some embodiments, the filler may also be removed from port system 270 with injector 295. Port membrane 273 is flexible and is configured to automatically seal itself after injector 295 is removed. By sealing itself, the filler can then be maintained in port system 270 and flexible member 280. Port membrane 273 may be made of silicone or other biocompatible materials of various thicknesses (>2 mm).

Flexible member 280 is in fluid and/or air communication with the filler delivered, maintained, or removed through the port system 270. In response to an increased pressure in port chamber 271 (e.g. when injector 295 is pushed), the filler flows into flexible member 280, and flexible member 280 inflates. In response to a decreased pressure in port chamber 271 (e.g., when injector 295 is pulled), the filler leaves flexible member 280, and flexible member 280 deflates. Flexible member 280 may have a shape that is suitable for introduction into paraglottic space 201. The shape and size of flexible member 280 may be adjustable by adding/removing filler to/from flexible member 280 via port system 270 during operation (intraoperatively). After the operation (postoperatively), in response to possible compromises, such as airway compromises, intubation difficulties, and others, the size of flexible member 280 may be readjusted to prevent the occurrences of complications.

Figure 2D:
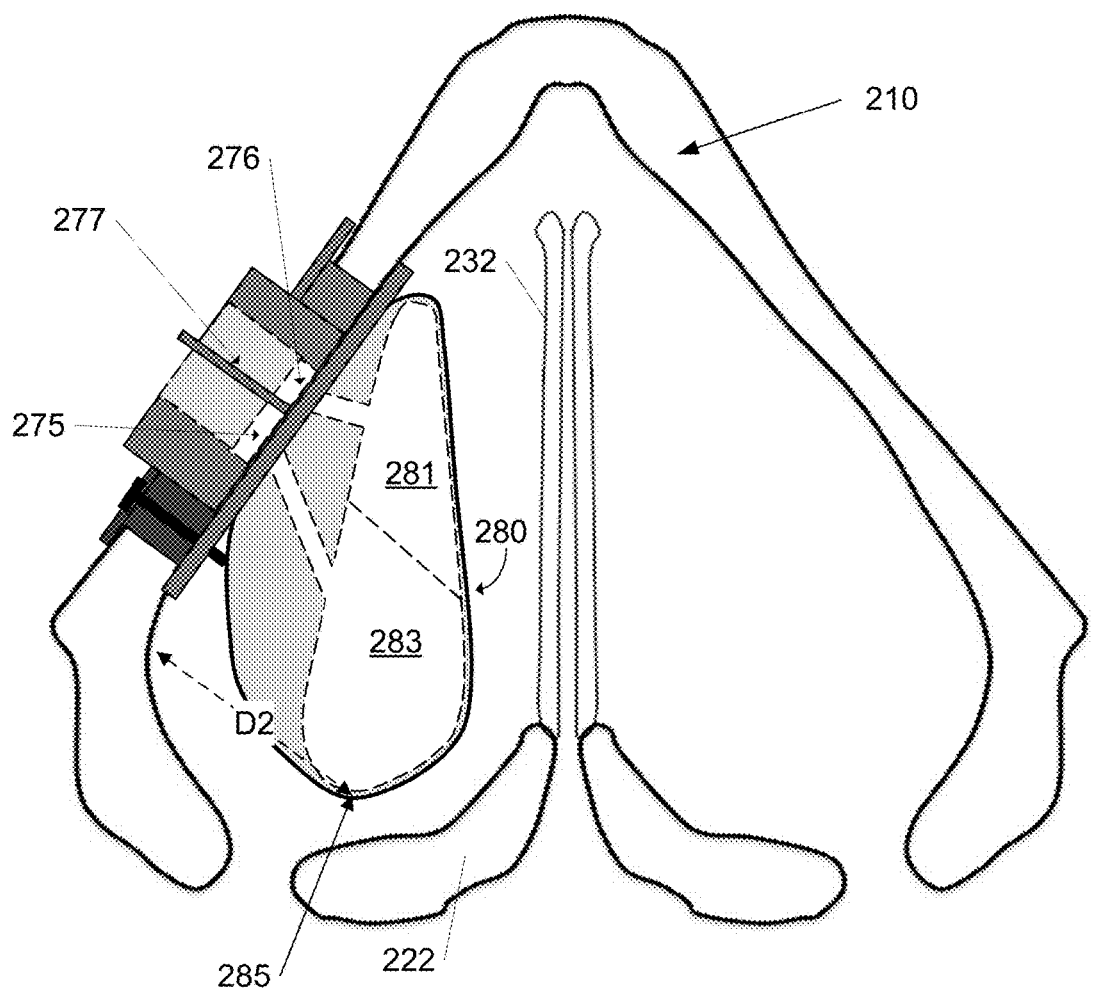
FIG. 2D illustrates an example embodiment of a flexible member of an implant system to treat glottic insufficiency, in accordance with some embodiments of the present disclosure.

FIG. 2D illustrates an example embodiment of flexible member 280 of implant system 200 to treat glottic insufficiency, in accordance with some embodiments of the present disclosure. In conjunction with FIG. 2C, in some embodiments, flexible member 280 includes anterior member 281 and posterior member 283. Anterior member 281 is in fluid and/or air communication with fillers maintained in first port chamber 276 of port system 270, and posterior member 283 is in fluid and/or air communication with fillers maintained in second port chamber 275 of port system 270. First port chamber 276 and second port chamber 275 are separated by pressure valve 277. Pressure valve 277 is configured to allow fillers to flow between first port chamber 276 and second port chamber 275 under a predetermined pressure. Inflations of anterior member 281 and posterior member 283 are controlled by the amount of fillers maintained in first chamber 276 and second chamber 275, respectively. Inflation of anterior member 281 may cause flexible member 280 to push paralyzed vocal fold 232 back to a median position. Inflation of posterior member 283 may cause flexible member 280 to push against arytenoid cartilage 222. The continued inflate of posterior member 283 would cause the adduction, rocking, and/or inferomedial rotation of arytenoid cartilage 222. Posterior member 283 may include a posterior-medial tip 285, which has a distance D2 of about 4 mm to about 15 mm measured perpendicularly from the medial side of the thyroid cartilage 210. Flexible member 280 is made of biocompatible materials, such as silicon or biodegradable materials. To support a designated expansion direction, flexible member 280 may be composed of a wall of varied stiffness (e.g., ≥20 Shore) and/or thickness (e.g., ≥2 mm).

Figure 2E:
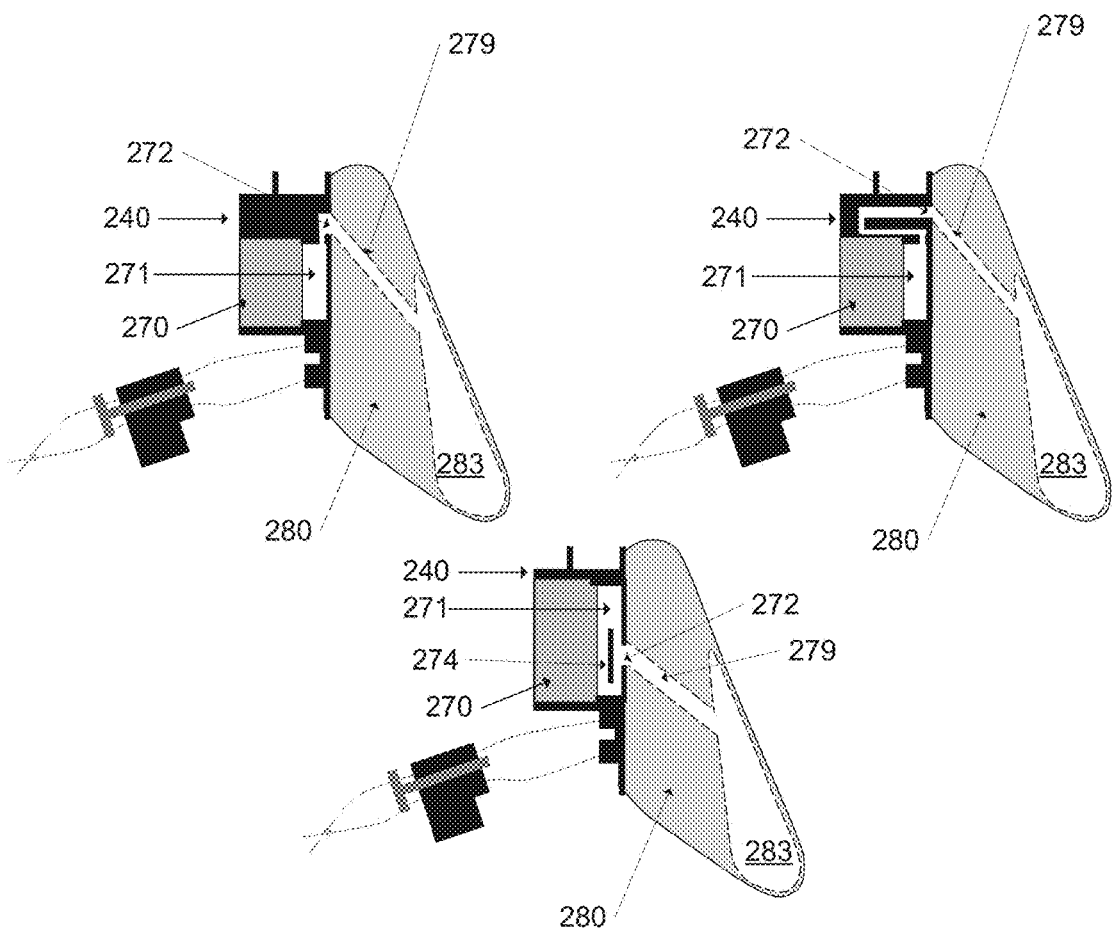
FIG. 2E illustrates example configurations of a flow channel of a port system within an implant system disposed between a port chamber of the port system and a posterior member of flexible member, in accordance with some embodiments of the present disclosure.

FIG. 2E illustrates example configurations of flow channel 279 of port system 270 disposed between port chamber 271 and posterior member 283 of flexible member 280, in accordance with some embodiments of the present disclosure. In conjunction with FIG. 2D, flexible member 280 may include posterior member 283 but not anterior member 281.

As illustrated, fixation frame 240 may have different configurations, and posterior member 283 is in fluid and/or air communication with port chamber 271 via flow channel 279. To prevent an injector configured to inject fillers into port system 270 from inadvertently puncturing flexible member 280 via flow channel 279, in some embodiments, as shown in the top two figures of FIG. 2E, flow channel 279 is disposed in manners such that its entry 272 cannot be directly accessed by the injector. For example, entry 272 may be disposed adjacent to one end of port chamber 271.

In an alternative embodiment, as shown in the bottom figure of FIG. 2E, fixation frame 240 includes rigid plate structure 274 extended from one side of port chamber 271, which is placed near entry 272, to prevent the injector from directly accessing entry 272.

Figure 3A:
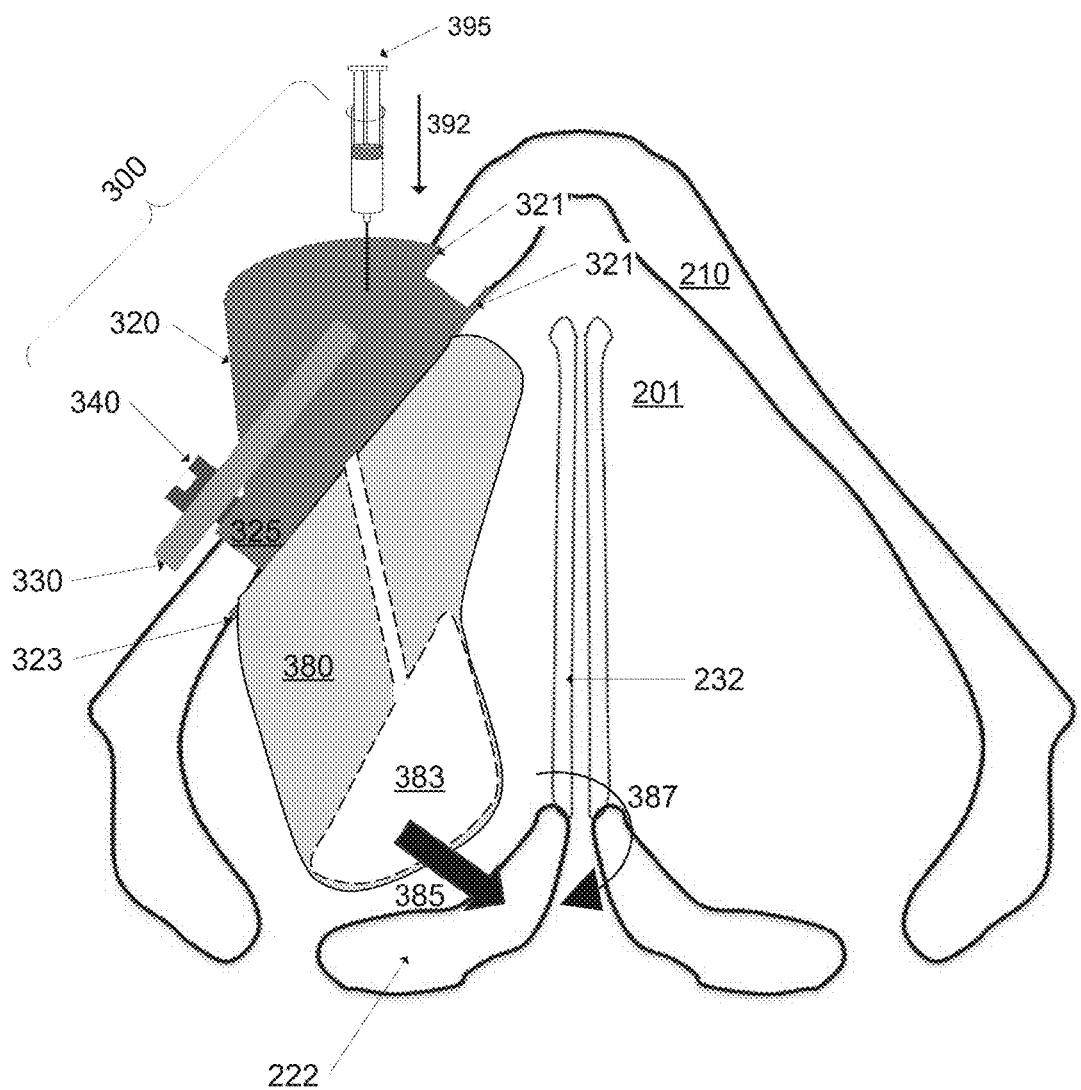
FIG. 3A illustrates a top view of an example implant system secured at a thyroid cartilage to treat glottic insufficiency, in accordance with some embodiments of the present disclosure.

In conjunction with FIG. 2A, FIG. 3A illustrates a top view of an example implant system 300 secured at thyroid cartilage 210 to treat glottic insufficiency, in accordance with some embodiments of the present disclosure. In contrast to implant system 200 illustrated in FIGS. 2B-2D, injector 395 is configured to deliver a filler to posterior member 383 of flexible member 380 in direction 392, causing posterior 383 to inflate approximately along direction 385 (e.g., inflate along the posterior-medial direction). Inserting injector 395 into implant system 300 in direction 392, as opposed to direction 292 shown in FIG. 2C, allows a healthcare professional to more easily and precisely access port system administer. As posterior member 383 inflates, it eventually comes into physical contact with arytenoid cartilage 222 and pushes against arytenoid cartilage 222 to initiate clockwise rotation 387 of arytenoid cartilage 222. While flexible member 380 and posterior member 383 may come in different shapes, they are configured to inflate in a particular manner, such as in a designated expansion direction (e.g., direction 385). As discussed earlier, the wall of a flexible member may be varied in stiffness and/or thickness to support a designated expansion direction. In other words, instead of inflating posterior member 383 and flexible member 380 uniformly in all directions, the wall of flexible member 380 may be less stiff/thinner in the proximity of arytenoid cartilage 222 but more stiff/thicker elsewhere, so that posterior member 383 and flexible member 380 mainly inflate in direction 385 as the filler continues to be delivered.

Additional details of implant system 300 are illustrated in FIGS. 3B-3E and described in the paragraphs below.

Figure 3B:
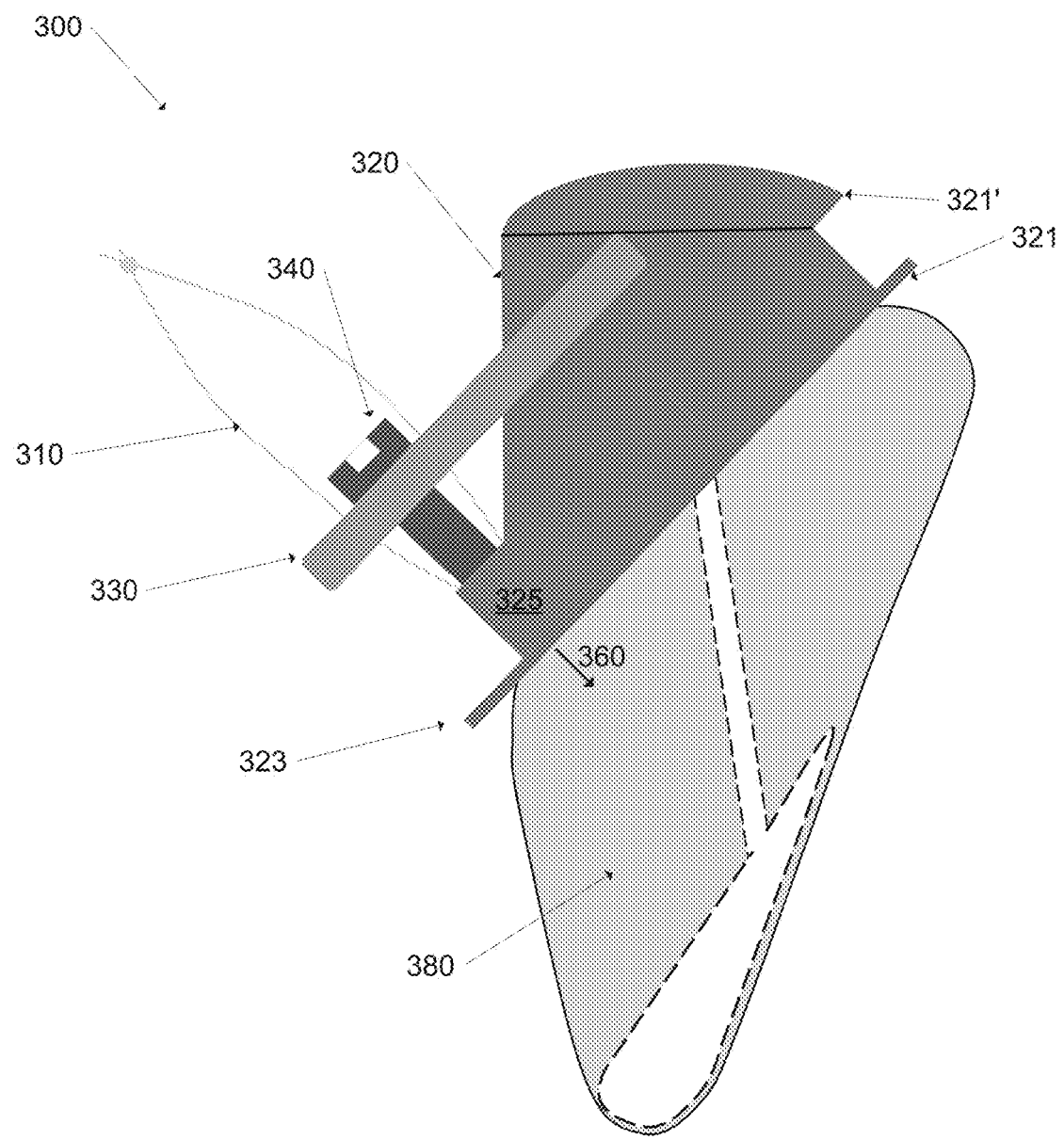
FIG. 3B illustrates an enlarged view of an example implant system configured to treat glottic insufficiency, in accordance with some embodiments of the present disclosure.

FIG. 3B illustrates an enlarged view of an example implant system 300 configured to treat glottic insufficiency, in accordance with some embodiments of the present disclosure. Implant system 300 includes, but not limited to, thread 310, fixation frame 320, fixation plate 330, screw 340, port system 350 (shown in at least FIGS. 3D and 3E), and flexible member 380.

In some embodiments, screw 340 is integrated with fixation plate 330. Fixation plate 330 may include holes so that thread 310 can go through them. One end of thread 310 may be attached to base 325 of fixation frame 320. Before screw 340 is fully engaged with base 325 and secures fixation plate 330 with base 325, fixation plate 330 with the integrated screw 340 may move along thread 310. With this illustrated configuration, thread 310 may help to ensure keeping fixation plate 330, screw 340, and fixation frame 320 together, especially during operation. Thread 310 may be removed after implant system 300 is secured at thyroid cartilage 210.

Fixation frame 320 is configured to secure implant system 300 at thyroid cartilage 210. Fixation frame 320 includes a first set of flanges 321 and 321'. Similar to flanges 241 shown in FIG. 2B, flanges 321 and 321' may be at a first edge of fixation frame 320 and separated from each other with a distance corresponding to the thickness D of thyroid cartilage 210. Flanges 321 and 321' may or may not be substantially in parallel. Fixation frame 320 may include biocompatible materials, for example, titanium, peek, or silicone. Fixation frame 320 may further include a second flange 323 at a second edge of fixation frame 320. Second flange 323 is configured to extend from the second edge of fixation frame 320 to cover opening 203 of thyroid cartilage 210.

In some embodiments, fixation frame 320 includes base 325 to receive screw 340. Base 325 is disposed adjacent to second flange 323 of fixation frame 320. Screw 340 may be secured in base 325. By securing screw 340 in base 325, fixation plate 330 and second flange 323 may hold thyroid cartilage 210 to secure implant system 300 at thyroid cartilage 210.

In some embodiments, screw 340 may protrude in direction 360, or medially, from second flange 323 with a certain distance and be physically in contact with flexible member 380. As screw 340 protrudes further from second flange 323, the distance of protrusion (not shown, but similar to D1 of FIG. 2C) increases. In some embodiments, the protrusion distance may be less than 5 mm. In other embodiments, the protrusion distance may be between 0 mm to about 4 mm. By pushing against flexible member 380 in medial or medioposterior direction, the change in the position of flexible member 380 creates a physical contact between flexible member 380 and arytenoid cartilage 222 and initiates a clockwise rotation of arytenoid cartilage 222. Similar to fastener 260 of FIG. 2C, this rotation leads to arytenoid cartilage 222 being rocked, adducted and/or rotated inferomedially, which results in having the paralyzed vocal fold 232 fixed in its median position.

Figure 3C:
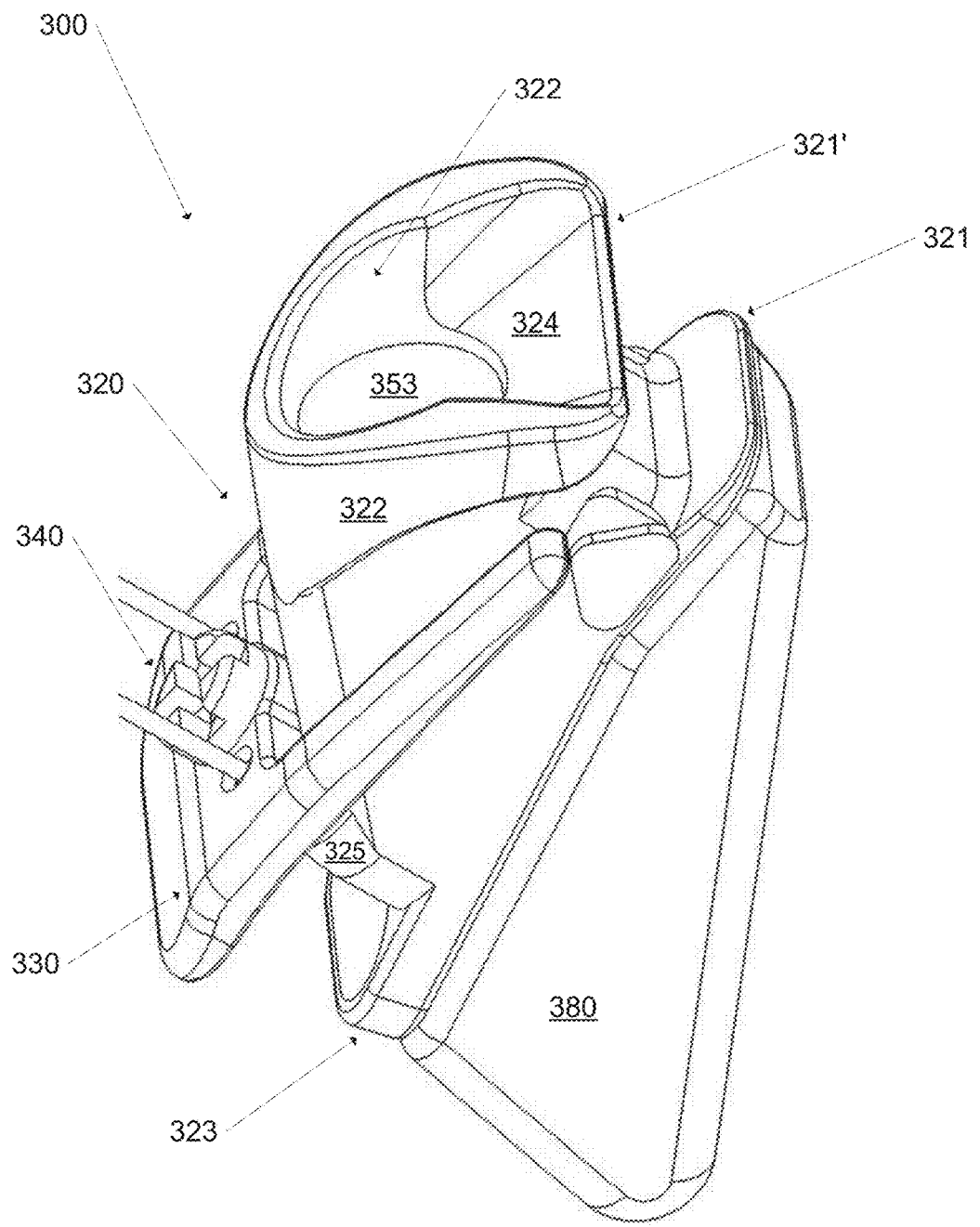
FIG. 3C illustrates a perspective view of an example implant system configured to treat glottic insufficiency, in accordance with some embodiments of the present disclosure.

FIG. 3C illustrates a perspective view of an example implant system 300 configured to treat glottic insufficiency, in accordance with some embodiments of the present disclosure. In conjunction with FIGS. 3A and 3B, in some embodiments, fixation frame 320 further includes a pair of side arms 322 and anterior shovel 324. Anterior shovel 324 may protrude anteriorly from port membrane 353, and anterior shovel 324 may also be substantially perpendicular with any of side arms 322. Anterior shovel 324 is disposed on one side of flange 321' at an angle substantially greater than 90 degrees. Anterior shovel 324 may be configured to guide injector 395 to reach port membrane 353 of port system 350. In some instances, anterior shovel 324 may also prevent injector 395 from puncturing the anterior aspect of a patient's larynx.

Side arms 322 help to define a boundary around port membrane 353 of port system 350. As injector 395 of FIG. 3A approaches port system 350, injector 395 may hit side arms 322, and the physical impact with side arms 322 may guide a surgeon to locate port membrane 353. Alternatively, side arms 322 may act as a visual guide for a surgeon to locate port system 350, because side arms 322 are visible as bright hyperechoic lines in ultrasound images. In some embodiments, the thickness of side arms 322 is between about 0.5 mm to about 2 mm.

Figure 3D:
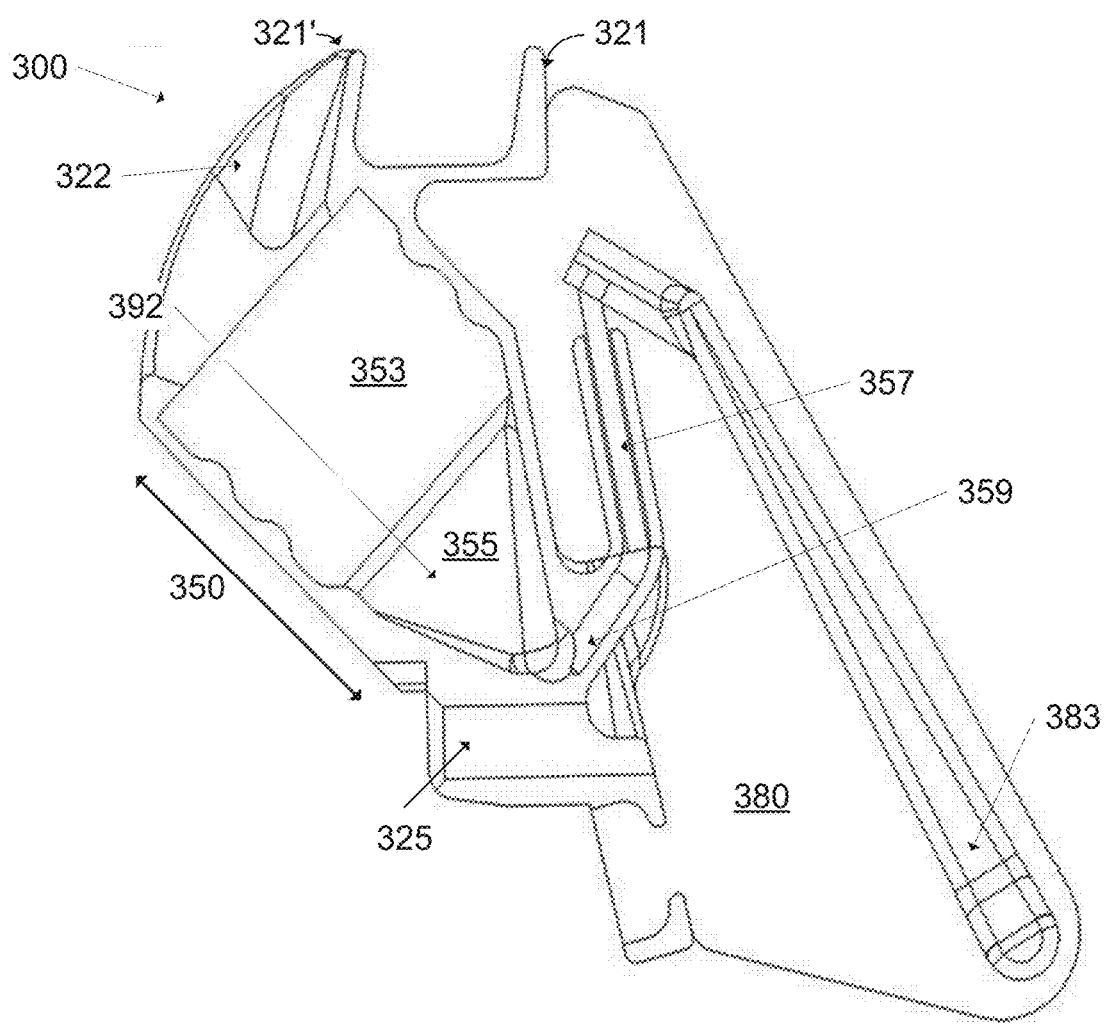
FIG. 3D illustrates a cross sectional view of an example implant system configured to treat glottic insufficiency, in accordance with some embodiments of the present disclosure.

FIG. 3D illustrates a cross sectional view of an example implant system 300, in accordance with some embodiments of the present disclosure. In conjunction with FIGS. 3A, 3B, and 3C, in some embodiments, port system 350 is an apparatus configured to receive, deliver, maintain, or remove one or more fillers to inflate, maintain or deflate posterior member 383 of flexible member 380. Port system 350 may be disposed in fixation frame 320 and may be adjacent to base 325. In some embodiments, port system 350 includes port membrane 353, port chamber 355, and flow channel 357. As injector 395 continues to move in direction 392, the needle of injector 395 may puncture port membrane 353 and move into port chamber 355. With the needle in port chamber 355, injector 395 may then inject fillers into port chamber 355. Posterior member 383 is in fluid and/or air communication with port chamber 355 via flow channel 357. In some embodiments, flow channel 357 is disposed in manners such that its entry 359 cannot be directly accessed by the needle of injector 395. For example, entry 359 may be disposed adjacent to one end of port chamber 355 to prevent injector 395 from inadvertently puncturing flexible member 380 via flow channel 357. The interior wall of port system 350 may have an undulated surface to prevent sliding of port membrane 353 when injector 395 is inserted into or removed from the port system 350.

Injector 395 is also visible as a bright hyperechoic line in response to injector 395 being inserted in the same plane as the ultrasound beam of the ultrasound scanner. The alignment of injector 395 and the ultrasound beam may be achieved by a mechanical guide attached to a probe of the ultrasound scanner. In some embodiments, a surface treatment is applied on the injector to increase the ultrasonic visualization. In some other embodiments, injector 395 may be an echogenic ultrasound needle. The echogenic ultrasound needle may include a polymer coating, which holds microbubbles and a dimpled shaft.

Figure 3E:
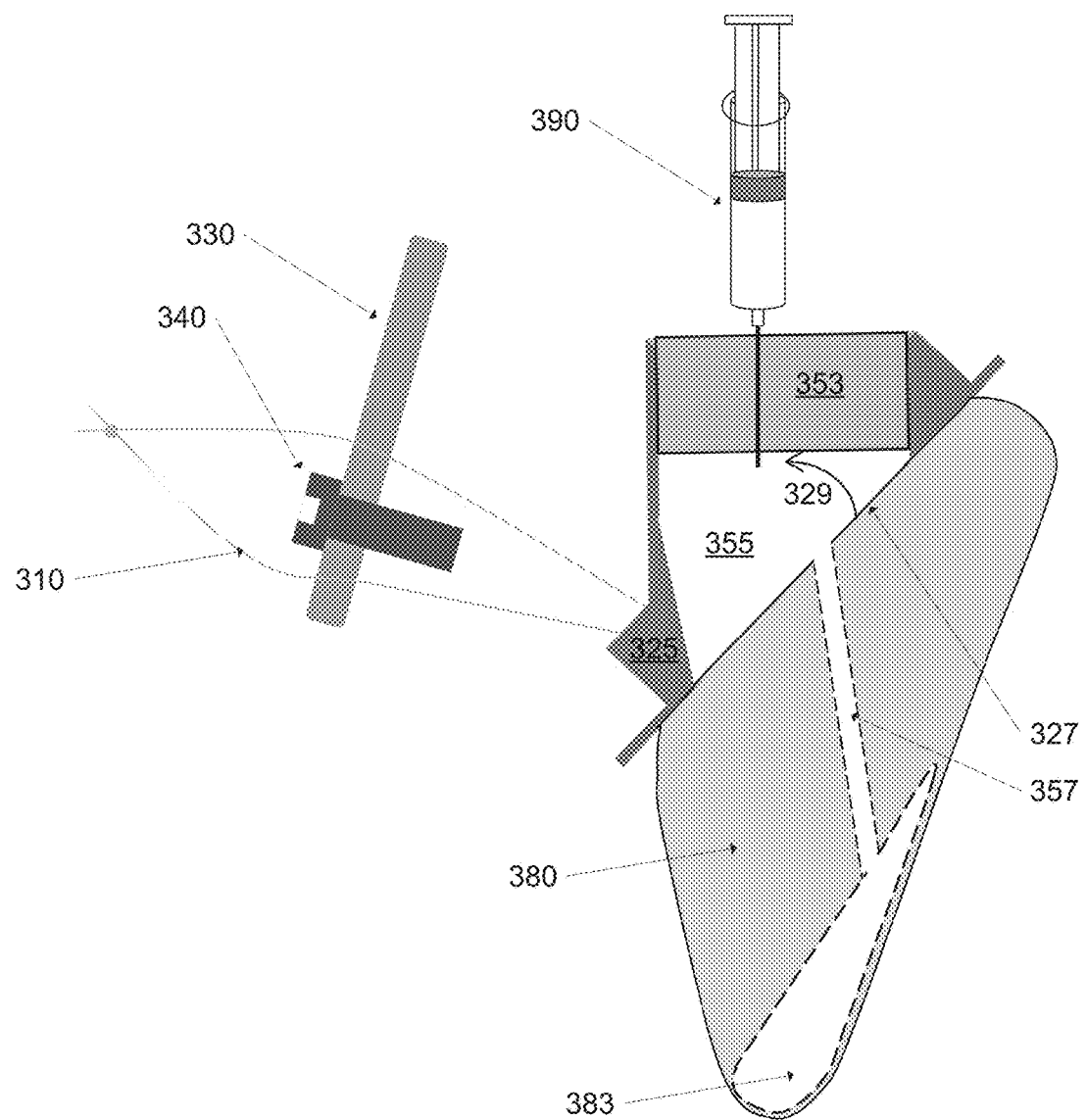
FIG. 3E illustrates an injection angle for an example implant system configured to treat glottic insufficiency, in accordance with some embodiments of the present disclosure.

FIG. 3E illustrates an injection angle for an example implant system 300 configured to treat glottic insufficiency, in accordance with some embodiments of the present disclosure. Port membrane 353 of the port system 350 and surface 327 of fixation frame 320 may define an injection angle 329 for injector 395 to inject one or more fillers into the port system 350. In some embodiments, injection angle 329 is about 0 degree to about 90 degrees. More specifically, injection angle 329 may be about 30 degrees to about 60 degrees (e.g., about 45 degrees). Orientation of the port membrane 353 and/or the port system 350 may be altered to adjust injection angle 329. In some embodiments, port membrane 353 and/or the port system 350 may be oriented uniaxially, biaxially, or triaxially to achieve a proper injection angle 329.

Figure 4:
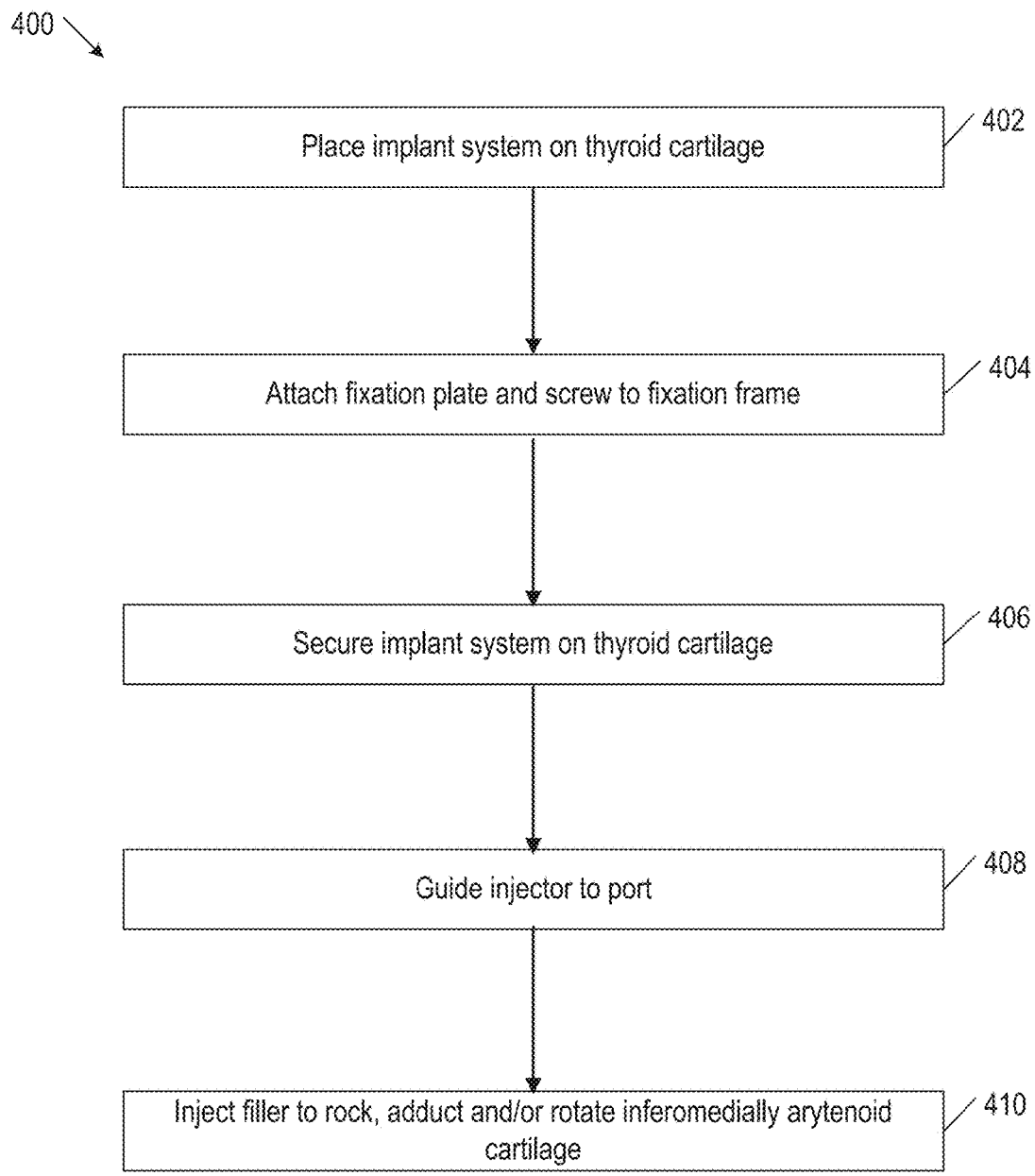
FIG. 4 illustrates a flow chart of an example process to treat glottic insufficiency with an example implant system, in accordance with some embodiments of the present disclosure.

FIG. 4 illustrates a flow chart of an example process 400 to treat glottic insufficiency with an example implant system 300, in accordance with some embodiments of the present disclosure. In conjunction with FIGS. 3A, 3B, 3C, and 3D, example process 400 may include one or more operations, functions, or actions illustrated by one or more blocks, such as 402 to 410. The various blocks may be combined into fewer blocks, divided into additional blocks, and/or eliminated depending on the desired implementation.

Example process 400 may begin in block 402. In block 402, implant system 300 is placed in an opening 203 on a patient's thyroid cartilage 210. As shown in FIG. 3A, flanges 321 and 321' are separated from each other with a distance corresponding to the thickness D of the thyroid cartilage so that flanges 321 and 321' are able to engage with the thyroid cartilage. Block 402 may be followed by block 404.

In block 404, fixation plate 330 and screw 340 are attached to fixation frame 320. In some embodiments, screw 340 is integrated with fixation plate 330. As discussed earlier, one end of thread 310 goes through one or more holes defined by fixation plate 330. The other end of thread 310 is attached to base 325 of fixation frame 320. Block 404 may be followed by block 406.

In block 406, implant system 300 is secured on thyroid cartilage. One securing mechanism is to fasten screw 340 to lock fixation plate 330 to base 325. In some embodiments, screw 340 may be fastened until the distance between fixation plate 330 and flange 323 substantially corresponds to the thickness D of the thyroid cartilage. In other embodiments, screw 340 may be turned further, so that screw 340 protrudes from base 325 and pushes against flexible member 380 in a medial or medioposterior direction. Block 406 may be followed by block 408.

In block 408, injector 395 is guided to port system 350. In some embodiments, side arms 322 are identified with ultrasonic waves to determine a boundary around the port system 350. Injector 395 may be also identified with ultrasonic waves to adjust the path of injector 395 to approach the port membrane 353 of the port system 350 according to identified side arms 322. In some embodiments, injector 395 is used to inject a filler into the port chamber 355 through the port membrane 353 of the port system 350. Port chamber 355 is in fluid/air communication with posterior member 383 of flexible member 380 via flow channel 381. In some embodiments, due to the injection angle of injector 395, injector 395 may come in physical contact with side arms 322 and/or anterior shovel 324. The feedback from the physical contact may cause a surgeon to adjust how injector 395 should be inserted and help to guide injector 395 to port membrane 353. Block 408 may be followed by block 410.

In block 410, certain amount of filler is injected by injector 395 so that the patient's arytenoid cartilage can be rocked, adducted, and/or rotated inferomedially. In some embodiments, posterior member 383 of flexible member 380 is adjusted based on the amount of the filler injected by injector 395. Posterior member 383 may inflate in response to an increased amount of the injected filler. Similarly, posterior member 383 may deflate in response to a decreased amount of the injected filler. The inflation and deflation of posterior member 383 may adduct and inferomedially rotate the arytenoid cartilage to place paralyzed vocal fold to a median position.

Thus, apparatuses and methods for treating glottic insufficiency have been disclosed. Although one or more embodiments of the present disclosure have been described in some detail for clarity of understanding, it will be apparent that certain changes and modifications may be made within the scope of the claims. Accordingly, the described embodiments are to be considered as illustrative and not restrictive, and the scope of the claims is not to be limited to details given herein, but may be modified within the scope and equivalents of the claims. In the claims, elements and/or steps do not imply any particular order of operation, unless explicitly stated in the claims.

Plural instances may be provided for components, operations or structures described herein as a single instance. Finally, boundaries between various components, operations and data stores are somewhat arbitrary, and particular operations are illustrated in the context of specific illustrative configurations. Other allocations of functionality are envisioned and may fall within the scope of the disclosure(s). In general, structures and functionality presented as separate components in exemplary configurations may be implemented as a combined structure or component. Similarly, structures and functionality presented as a single component may be implemented as separate components. These and other variations, modifications, additions, and improvements may fall within the scope of the appended claims(s).

We claim:

1. An implant system to treat glottic insufficiency of a patient, comprising:
    a fixation frame comprising a first set of flanges at a first edge of the fixation frame, a second flange at a second edge of the fixation frame, and a set of side arms, wherein the fixation frame is configured to secure the implant system at an opening of the patient's thyroid cartilage, wherein the second flange is configured to extend from the second edge away from the first edge to cover the opening of the patient's thyroid cartilage;
    a port system disposed in the fixation frame and configured to deliver, maintain or remove a filler, wherein the port system includes a port membrane, and the port system is configured to prevent sliding of the port membrane, wherein the set of side arms form a boundary around the port membrane of the port system;
    a shovel disposed on one of the first set of flanges at an angle, wherein the shovel protrudes anteriorly from the port system; and
    a flexible member, coupled to the fixation frame and in fluid or air communication with the port system, wherein based on an amount of the filler in the flexible member, the flexible member is configured to inflate in a direction to push against the patient's arytenoid cartilage so the arytenoid cartilage can be rocked, adducted and/or rotated inferomedially.

2. The implant system of claim 1, wherein the first set of flanges are separated from each other with a distance corresponding to a thickness of the patient's thyroid cartilage.

3. The implant system of claim 1, further comprises:
    a fixation block; and
    a fastener, wherein the fastener is configured to secure the fixation block to the second flange of the fixation frame.

4. The implant system of claim 3, wherein the fixation block comprises a third flange, and after the fastener is fastened to the second flange, a distance between the second flange and the third flange corresponds to a thickness of the patient's thyroid cartilage.

5. The implant system of claim 3, wherein the fastener is configured to push the flexible member through the second flange to further rock, adduct and inferomedially rotate the patient's arytenoid cartilage.

6. The implant system of claim 1, wherein the fixation frame defines an opening to receive one or more sutures having a first end to be in physical contact with the patient's arytenoid cartilage, intrinsic laryngeal adductor muscles, or arytenoid cartilage and intrinsic laryngeal adductor muscles, or a second end secured at a fastener disposed adjacent to the opening.

7. The implant system of claim 1, wherein the flexible member comprises an anterior member or a posterior member,
    wherein the anterior member is in fluid or air communication with the filler maintained in a first port chamber defined by the port system, and in response to the filler flowing in the anterior member from the first port chamber, the anterior member is inflated, causing the flexible member to push the patient's vocal fold medially, and
    wherein the posterior member is in fluid or air communication with the filler maintained in a second port chamber defined by the port system, and in response to the filler flowing in the posterior member from the second port chamber, the posterior member is inflated, causing the flexible member to push the patient's arytenoids cartilage so the patient's arytenoids cartilage can be adducted, rocked, and/or inferomedially rotated.

8. The implant system of claim 7, wherein the port system further comprises a flow channel with an entry of the flow channel disposed adjacent to an end of the second port chamber.

9. The implant system of claim 7, further comprises a plate placed near an entry of a flow channel in the port system.

10. The implant system of claim 1, further comprises:
a base disposed adjacent to the first edge of the fixation frame;
a fixation plate configured to secure with the base and hold the patient's thyroid cartilage with the second flange; and
a fastener integrated with the fixation plate to secure the fixation plate to the base.

11. The implant system of claim 10, further comprising a thread with an end attached to the base, wherein the fixation plate includes one or more holes for the thread to go through.

12. The implant system of claim 1, wherein the side arms are made of a material responsive to an ultrasound and visible as bright hyperechoic lines in an ultrasound image.

13. The implant system of claim 1, wherein the side arms are disposed adjacent to a second edge of the fixation frame.

14. The implant system of claim 1, wherein the shovel is configured to guide an injector to the port membrane.

15. The implant system of claim 1, wherein the port membrane and a surface of the fixation frame defines an angle of about 0 degree to about 90 degrees to deliver the filler to the port system.

16. The implant system of claim 1, wherein the port system further comprises:
a port chamber; and
a flow channel, wherein the flow channel includes an entry disposed adjacent to an end of the port chamber.

17. The implant system of claim 16, wherein an interior wall of the port system has an undulated surface.

18. The implant system of claim 1, wherein the flexible member comprises a posterior member in fluid or air communication with the filler maintained in a port chamber defined by the port system, and in response to the filler flowing in the posterior member from the port chamber, the posterior member is inflated along a posterior-medial direction, causing the flexible member to push against the patient's arytenoids cartilage so the patient's arytenoids cartilage can be adducted, rocked, and/or inferomedially rotated.

19. The implant system of claim 18, wherein the flexible member is composed of a wall of varied stiffness and/or thickness to support expansion in the posterior-medial direction.

* * * * *